United States Patent [19]

Ohashi et al.

[11] Patent Number: 4,483,873
[45] Date of Patent: Nov. 20, 1984

[54] AQUEOUS SOLUTION CONTAINING UBIDECARENONE

[75] Inventors: Hiroyuki Ohashi; Toru Takami, both of Kanagawa; Noritoshi Koyama, Saitama; Yoshio Kogure, Saitama, Japan; Katsumi Ida, Saitama, all of Japan

[73] Assignee: Eisai Co., Ltd., Tokyo, Japan

[21] Appl. No.: 452,844

[22] Filed: Dec. 23, 1982

[30] Foreign Application Priority Data

Dec. 28, 1981 [JP] Japan .................................. 56-209972

[51] Int. Cl.$^3$ .................. A61K 31/12; A61K 31/685; A61K 37/48
[52] U.S. Cl. ..................................... 424/331; 424/94; 424/199

[58] Field of Search ........................... 424/94, 199, 331

[56] References Cited

U.S. PATENT DOCUMENTS 4,068,001  1/1978  Kanno ................................... 424/94
4,325,942  4/1982  Taki et al. ............................. 424/94

OTHER PUBLICATIONS

The Merck Index, 9th ed., item 5287 (1976).

*Primary Examiner*—Douglas W. Robinson
*Attorney, Agent, or Firm*—Wenderoth, Lind & Ponack

[57] ABSTRACT

An aqueous solution containing ubidecarenone which is characterized by the fact that a hydrogenated lecithin is incorporated. This solution is stable and free side effects.

4 Claims, No Drawings

AQUEOUS SOLUTION CONTAINING UBIDECARENONE

BACKGROUND OF THE INVENTION

1. Field of the Invention

The present invention relates to aqueous solutions containing ubidecarenone. More specifically, it relates to aqueous solutions containing ubidecarenone in which a hydrogenated lecithin is incorporated.

2. Description of the Prior Art

Ubidecarenone (hereinafter referred to as $CoQ_{10}$) is a substance which has been biochemically found to be involved in the myocardiac mitochondrial electron transport system and to play an important role in the production of energy. It has been found clinically to be effective in the improvement of congestive conditions, anginal conditions, etc., caused by the reduction in cardiac functions, such as chronic hypertension, ischemic disease, valvular disease, etc., and has come into wide clinical use. Said substance has heretofore been in the market often in the form of a solid preparation solely for oral administration, and this form itself has enabled the sufferer to take doses easily and has contributed to achieving a wide use of said substance.

In recent years, however, as a wider range of application of said substance has been discovered, it has been determined that the substance is more favorably presented as an aqueous solution. For example, the substance is poor in absorption through the intestinal track [*Chem. Pharm. Bull.*, 20, 2585 (1972)], and it is clinically desired to administer orally as an aqueous syrup or to administer as an injectable preparation comprising an aqueous solution. It is also desirable that this should be administered as an aqueous topical preparation in pursuit of a therapeutic effect in the dermatological field.

However, $CoQ_{10}$ is a lipid-soluble substance having a melting point of 48°–52° C. and is in the solid state an normal temperature. It is very difficult to be solubilized in water. Therefore, the present situation is such that a satisfactory aqueous preparation of the substance has not yet been obtained. For making it soluble in water, there has been a conventional method which comprises utilizing a nonionic surfactant, such as HCO-60 (produced by Nikko Chemical Co., Ltd.), but this requires a large amount of HCO-60, and as a result, when administered as an injectable preparation, it leads to the liberation of a histamine-like substance, and also when administered as an oral preparation, it brings about difficulty in the digestive tract and exhibits undesirable side effects such as diarrhea, etc.

Under such circumstances, the object of the present invention is to provide aqueous solutions containing $CoQ_{10}$ which are prepared without using a nonionic surfactant such as HCO-60.

SUMMARY OF THE INVENTION

Accordingly, the present invention relates to aqueous solutions containing $CoQ_{10}$ which are characterized by incorporating a hydrogenated lecithin.

DETAILED DESCRIPTION OF THE PREFERRED EMBODIMENTS

The primary feature of the aqueous solutions of the present invention is that said aqueous solutions do not considerably change their transparent or slightly turbid conditions with time. That is, when the aqueous solution is measured for transmittance ($T_{640}$) at 640 nm immediately after production and after, e.g., 13 days at 60° C., and the percent change in transmittance (%) as defined below is calculated, it has a feature that said percent change is small.

Percent Change in Transmittance (%) =

$$\frac{T_{640} \text{ (Immediately after the Production)} - T_{640} \text{ (After 13 Days at 60° C.)}}{T_{640} \text{ (Immediately after the Production)}} \times 100$$

The second feature of the aqueous solutions of the present invention is that said aqueous solutions do not exhibit considerable coloration with time. Although whether the cause for the coloration is $CoQ_{10}$ itself or the hydrogenated lecithin is not clarified, those which develop coloration with time are not preferred as products. Therefore, when the aqueous solution is measured for the transmittance ($T_{560}$) at 560 nm immediately after the production and after 13 days at 60° C., and the percent change in coloration (%) as defined below is calculated, it has a feature that said percent change is small.

Percent Change in Coloration (%) =

$$\frac{T_{560} \text{ (Immediately after the Production)} - T_{560} \text{ (After 13 Days at 60° C.)}}{T_{560} \text{ (Immediately after the Production)}} \times 100$$

Accordingly, the present invention provides aqueous solutions containing $CoQ_{10}$ in which the aforesaid percent change in transmittance and percent change in coloration are small in accordance with the requirements of the invention, which will be more particularly described hereinbelow.

The hydrogenated lecithin according to the present invention is a lecithin, the resistance to oxidation of which has been enhanced by hydrogenation. More specifically, examples include hydrogenated soybean lecithin, hydrogenated ovolecithin, etc., among which hydrogenated soybean lecithin is especially preferred. These hydrogenated lecithins are preferably those containing 85% or more of phospholipid components and having an iodine value of 10–60, especially 25–50. This is because if it exceeds 60, the lecithin itself is extremely hardened, and the operation to coarsely disperse is practically difficult. Whereas, with the value of less than 10, the effect of the present invention cannot be expected. As the phospholipid, that having a high content of phosphatidyl choline, for example, in the case of soybean phospholipid, that in which 80–95% of phosphatidyl choline is contained and in addition lysolechithin and phosphatidyl ethanolamine are detected is satisfactory. That which is especially preferred is the hydrogenated lecithin described in Japanese Patent Application Laid-open Nos. 83911/1977 and 62010/1980.

The amounts of the $CoQ_{10}$ and hydrogenated lecithin to be incorporated in the aqueous solutions of the present invention are as follows:

In the first place, clinically, the concentration of $CoQ_{10}$ required in an aqueous solution is 0.1–10% and, in general, 0.2–0.5% is frequently employed. Especially, in the case where the aqueous solution is used as an injectable preparation, 0.2% or so is often employed. On the other hand, $CoQ_{10}$ is often injected into a sugar transfusion and used as a co-infusion material together with the sugar transfusion. In such a case, the concentration is lower than the aforesaid range. However, since observation reveals that the dilution used in a sugar transfusion does not immediately affect the solubilization, the concentration to be aimed at may be established with the aforesaid range. However, it is clear that the present invention is not particularly restricted to said range.

The amount of the hydrogenated lecithin to be incorporated varies depending on the purpose of the use of the aqueous solution, and, where it is desired that the aqueous solution is transparent from an aspect of its desired use, the hydrogenated lecithin is preferably added in an amount of 1-5 parts by weight per part by weight of $CoQ_{10}$. However, where some degree of turbidity of the aqueous solution is allowed, 0.2-1 part by weight of 5-15 parts by weight may also be sufficient. Therefore, practically 0.2-15 parts by weight of the hydrogenated lecithin may be incorporated per part by weight of $CoQ_{10}$. However, there is no reason why this invention should be restricted to said range.

In the aqueous solutions of the present invention, a part of the water may be replaced by a water-soluble solvent such as propylene glycol, low molecular weight polyethylene glycol, glycerol, etc. These solvents have an effect to greatly shorten the time required for coarsely dispersing $CoQ_{10}$ uniformly on production. That is, by coarsely dispersing $CoQ_{10}$ in a water-soluble solvent using a hydrogenated lecithin instead of directly mixing $CoQ_{10}$ and the hydrogenated lecithin, and thereafter by adding water, the time required for solubilization may be shorter. However, such a water-soluble solvent is merely conveniently employed on the production of the aqueous solutions of the present invention, and the object of the present invention may of course be achieved even when it is not added. Therefore, the present invention is not restricted by the addition of these solvents.

In the case where the water-soluble solvent is added in order to facilitate the production, the amount thereof to be added is 20-50 parts by weight per part by weight of $CoQ_{10}$ and may sufficiently be 2-10% based on the aqueous solution of the present invention.

Further, when the aqueous solution of the present invention is used as an injectable preparation, it is possible to add additives commonly frequently employed as isotonizing agents, for example, sugars and/or sugar alcohols, such as glucose, xylite, sorbite, mannite, etc. That is, the addition of these isotonizing agents does not interfere with the characteristics of the present invention and is rather effective against the formation of turbidity on the sterilization of the injectable preparation. The amount of these additives to be incorporated is preferably 1-10% based on the aqueous solution of the present invention.

The production of the aqueous solutions of the present invention may be carried out as follows. First, a small amount of water is added, then $CoQ_{10}$ and a hydrogenated lecithin are added thereto and coarsely dispersed uniformly by warming to a temperature above the melting point of $CoQ_{10}$, particularly to 60-70° C.. For dispersing, it is preferred to carry out pressurizing treatment or ultrasonic treatment at the same time with stirring, thereby achieving forced dispersion. Further, by using a water-soluble solvent such as propylene glycol, polyethylene glycol, glycerol, etc., instead of water, coarse dispersion is even further facilitated. Additional components and the remaining water are added to the resultant coarse dispersion and uniformly dispersed to obtain an aqueous solution of the present invention. Where the aqueous solution of the present invention is to be made into an injectable preparation, it is filtered, filled into predetermined ampules and sterilized. The additional components may freely be chosen among, for example, a buffer, a sterilizing agent, an isotonizing agent, etc., but the addition of an electrolyte component should preferably be avoided because it would destroy the dispersed conditions, particularly the solubilized conditions.

The hydrogenated lecithin may be produced by adding lecithin to an autoclave, then adding a solvent and a catalyst, bringing them into contact with hydrogen and continuing the hydrogenation until the desired iodine value is obtained. After the reaction, the catalyst is filtered off and the solvent is distilled off to obtain the hydrogenated lecithin.

The hydrogenated lecithin to be employed in the present invention is particularly preferably a hydrogenated lecithin which has been treated by special purification as described in the aforesaid Japanese Patent Application Laid-open No. 62010/1980.

The present invention is more particularly described by the examples given below, but it should be noted that the invention is not restricted to those.

EXAMPLE 1

Hydrogenated soybean lecithin (220 mg) and 20 ml of water were added to 250 mg of $CoQ_{10}$ and mixed by warming at 65° C., followed by ultrasonic treatment (20 KH, 200 W) under $N_2$ gas for 90 minutes to obtain an aqueous solution. Sorbite (5 g) and water were added thereto to make the total volume 100 ml, filtered through a membrane filter, and 2 ml portions were filled into ampules under $N_2$ gas and sealed. This was followed by sterilization of the ampules at 110° C. for 30 minutes to prepare $CoQ_{10}$ containing injectable preparations.

EXAMPLE 2

Hydrogenated soybean lecithin (220 mg), 5 g of propylene glycol and 15 ml of water were added to 250 mg of $CoQ_{10}$ and mixed by warming at 65° C., followed by ultrasonic treatment (20 KH, 200 W) under $N_2$ gas for 5 minutes to obtain a coarse dispersion. Water was added thereto to make the total volume 90 ml and ultrasonic treatment (20 KH, 200 W) was conducted for 40 minutes. Further, 5 g of sorbite and water were added thereto to make the total volume 100 ml, and thereafter procedures similar to those in Example 1 were conducted to obtain $CoQ_{10}$ containing injectable preparations. By using the ultrasonic treatment in this example it was possible to shorten the time required for forming the solution to half the time of that of Example 1.

EXAMPLE 3

Hydrogenated ovolecithin (50 mg), amounting to 0.2 parts by weight per part by weight of $CoQ_{10}$ and 20 ml of water were added to 250 mg of $CoQ_{10}$ and mixed by warming at 65° C., followed by ultrasonic treatment (20 KH, 200 W) under $N_2$ gas for 120 minutes to obtain an aqueous solution. Sorbite (20 g), 100 mg of methylparaben, vanilla essence and water were added thereto to make the total volume 100 ml to prepare a syrup containing $CoQ_{10}$. Said syrup was slightly turbid, but no change in turbidity or coloration was observed after 30 days at 45° C.

EXAMPLE 4

Hydrogenated soybean lecithin (3 g), amounting to 15 parts by weight per part by weight of $CoQ_{10}$ and 4 g of glycerol were added to 200 mg of $CoQ_{10}$ and mixed by warming at 65° C. Then 15 mol of water was added, followed by dispersing on a high-speed stirrer under $N_2$ gas for 50 minutes. Then, 5 g of sorbite, 10 g of ethanol and water were added thereto to make the total volume 100 ml to prepare a topical liquid preparation containing $CoQ_{10}$.

The effect of the present invention is now described by the following Examples of Effect.

EXAMPLE OF EFFECT 1

Samples and Method

Each of the four kinds of the lecithins set forth in Table 1 (100 mg each) and 20 ml each of water were added to 100 mg each of $CoQ_{10}$, mixed by warming and subjected to ultrasonic treatment to obtain coarse dispersions respectively. Further, 5 g of sorbite and water were added to each dispersion to make the total volume 100 ml, then each mixture was subjected again to ultrasonic treatment, filtered, filled into 20 ml ampules under $N_2$ gas and sealed. The ampules were sterilized at 115° C. for 30 minutes to obtain samples, respectively. $T_{640}$ and $T_{560}$ values were measured on each sample immediately after the production and after 13 days at 60° C., to determine the percent change in transmittance and the percent change in coloration.

Results

The results are given in Table 1.

TABLE 1

| Lecithin | Percent change in Transmittance | Percent change in Coloration |
|---|---|---|
| Ovolecithin | | |
| Non-hydrogenated | 40.0 | 46.7 |
| Hydrogenated | 0.4 | 1.1 |
| Soybean Lecithin | | |
| Non-hydrogenated | 12.1 | 17.8 |
| Hydrogenated | 0.8 | 1.2 |

The numerical values in the Table indicate %. The iodine value of the hydrogenated lecithin used is 40 and its phospholipid content is 90%.

From Table 1, it can be seen that the percent changes in transmittance and coloration with time are greater in the case of the non-hydrogenated lecithin both with ovolecithin and soybean lecithin. Where hydrogenated lecithins were employed, the values are significantly improved.

EXAMPLE OF EFFECT 2

Samples and Method

The four kinds of lecithins set forth in Table 2 below were each added in amounts of 250 mg (1 part by weight per part by weight of $CoQ_{10}$) or 1 g (i.e., 4 parts by weight) to 250 mg each of $CoQ_{10}$ along with 20 ml each of water, mixed by warming, and thereafter procedures similar to those in the section of Samples and Method in Example of Effect 1 were conducted to prepare samples, respectively, and the percent change in transmittance and the percent change in coloration were determined.

Results

The results are given in Table 2.

TABLE 2

| | | Amount of Lecithin | | | |
|---|---|---|---|---|---|
| | | 1 Part by Weight | | 4 Parts by Weight | |
| | Lecithin | % Change in Transmittance | % Change in Coloration | % Change in Transmittance | % Change in Coloration |
| Ovo-lecithin | Non-hydrogenated | 7.9 | 15.3 | Not Measurable | Not Measurable |
| | Hydrogenated | 0.7 | 2.4 | 3.4 | 6.1 |
| Soybean Lecithin | Non-hydrogenated | 73.4 | 41.4 | 57.4 | 63.0 |
| | Hydrogenated | 0 | 0.3 | 0.8 | 1.5 |

The numerical values in the table indicate %, and the "Not Measurable" means that the measurement was not possible due to the formation of precipitates. The "Amount of Lecithin" means the amount per part by weight of $CoQ_{10}$. The iodine value of the hydrogenated lecithin used is 42 and its phospholipid content is 88%.

From Table 2, facts similar to those described in the section of Results in Example of Effect 1 are found.

As clear from the above-described Examples of Effect, the aqueous solutions of $CoQ_{10}$ according to the present invention have a significant effect in that they are stable and free from side effects.

What is claimed is:

1. An aqueous pharmaceutical solution comprising 0.1 to 10% ubidecarenone and 0.2 to 15 parts by weight per part by weight of ubidecarenone of a hydrogenated lecithin containing at least 85% of phospholipid components and having an iodine value of 10 to 60.

2. An aqueous pharmaceutical solution according to claim 1 which also contains (a) 20 to 50 parts by weight per part by weight of ubidecarenone of a water-soluble solvent, the solvent corresponding to 2 to 10% based on the aqueous solution, and (b) 1 to 10% of an isotonizing agent based on the aqueous solution, or a mixture of the solvent and the isotonizing agent.

3. An aqueous solution according to claim 2 wherein the water-soluble solvent is a member selected from the group consisting of propylene glycol, low molecular weight polyethylene glycol and glycerol.

4. An aqueous solution according to claim 2 wherein the isotonizing agent is a member selected from the group consisting of glucose, xylite, sorbite and mannite.

* * * * *